United States Patent [19]

Vidra

[11] 4,360,512

[45] Nov. 23, 1982

[54] NONABRASIVE GEL FORMULATIONS OF SULFONATED POLY(ARYLENE ETHER SULFONE) POLYMER DENTAL PLAQUE BARRIERS

[75] Inventor: James D. Vidra, Clinton, N.J.

[73] Assignee: Johnson & Johnson Products Inc., New Brunswick, N.J.

[21] Appl. No.: 172,350

[22] Filed: Jul. 25, 1980

[51] Int. Cl.³ .................. A61K 7/16; A61K 7/22; A61K 31/315; A61K 31/185
[52] U.S. Cl. .................. 424/56; 424/54; 424/78; 424/289; 424/315; 424/316
[58] Field of Search .................. 424/49–52, 424/78, 315; 260/505 R, 512

[56] References Cited

U.S. PATENT DOCUMENTS

| | | | |
|---|---|---|---|
| 3,709,841 | 1/1973 | Quentin | 260/2.2 R |
| 3,855,122 | 12/1974 | Bourganel et al. | 264/49 |
| 3,875,096 | 4/1975 | Graefe et al. | 260/29.2 N |
| 3,919,429 | 11/1975 | Grossmann et al. | 424/78 |
| 3,954,677 | 5/1976 | Law | 260/505 R |

FOREIGN PATENT DOCUMENTS

| | | | |
|---|---|---|---|
| 1960812 | 12/1969 | Fed. Rep. of Germany | 260/512 |
| 1296952 | 11/1972 | United Kingdom. | |
| 1507772 | 4/1978 | United Kingdom. | |

OTHER PUBLICATIONS

Polymer 18, 354–374 (1977)–Attwood et al.
J. Polymer Sci., Part A-1, vol. 5, 2375–2398 (1967), Johnson et al.
J. Applied Poly. Sci. 20, 1885–1903 (1976)–Noshay et al.
Desalination 18, 137–153 (1976)–Brousse et al.
International Publication #WO79/00456–1979–Chang.

Primary Examiner—Douglas W. Robinson

[57] ABSTRACT

Compositions for preventing the attachment of dental plaque to the surfaces of the teeth comprise certain sulfonated poly(arylene ether sulfone) polymers and the pharmaceutically acceptable salts thereof in a pharmaceutically acceptable nonabrasive gel vehicle comprising a selected polyoxypropylene/polyoxyethylene block copolymer as the principal gelling agent.

6 Claims, No Drawings

NONABRASIVE GEL FORMULATIONS OF SULFONATED POLY(ARYLENE ETHER SULFONE) POLYMER DENTAL PLAQUE BARRIERS

TECHNICAL FIELD

This invention relates to a oral hygiene compositions and methods using such compositions to prevent attachment of bacteria to teeth. More particularly, it relates to certain nonabrasive gel compositions comprising selected sulfonated polymeric materials that have been found useful in inhibiting the agglutination of oral microbes on teeth, wherein the principal gelling agent is a selected block copolymer of polyoxypropylene and polyoxyethylene.

BACKGROUND ART

The prevention of the deposition of dental plaque on teeth is a highly desired result. Dental plaque results when cariogenic bacteria aggregate in colonies on the surface of teeth and form a tenacious deposit thereon. The presence of plaque on teeth is believed to be a precursor to development of gingivitis, dental caries and periodontal disease.

While many attempts have been made to control the effects of cariogenic bacteria and the dental plaque they produce, for example, fluoride, flossing, brushing, etc., treatments, these are typically directed to either counteracting the secondary effects of plaque on the teeth and gums, or to the removal of plaque that is already formed on and adhering to the teeth and surrounding tissue. Such treatments are not, however, entirely successful, and must be supplemented with periodic treatment by dental professionals. To date, there is no commercially feasible home treatment method for preventing the formation of plaque or its adhesion to teeth.

A number of hydrophilic sulfonic acid and sulfonic acid salt derivatives of certain poly (arylene ether sulfone) polymers have been synthesized and found to inhibit the deposition of dental plaque onto human teeth. These sulfonated polymers have good film forming properties. They are anionic in nature and partially soluble in water or water/organic solvent vehicles, primarily because of the relatively high degree of sulfonation achieved during preparation of these derivatives. While the mechanism of action of the hydrophilic polymeric films in retarding plaque deposition is not known with absolute certainty, it is presumed that the films of anionically-charged polymers deposited on teeth effect a mutual repulsion between the negatively charged polymer film and the negatively charged microorganisms in oral fluids responsible for plaque generation. For example, when powdered human dental enamel is dispersed in the aqueous media containing salts of the polymeric sulfonates, a substantially negative surface charge is imparted to the enamel particles, as determined by zeta potential measurements.

THE INVENTION

While attempting to formulate these sulfonated polymers into aesthetically acceptable oral hygiene compositions, a number of formulation compatibility problems were encountered. The incompatibility was manifested by precipitation of the sulfonated polymer whenever high polymer concentrations were formulated into mouthrinse vehicles. This incompatibility also was evident from low plaque barrier activity readings from in vitro tests on several vehicle forms. Several dentifrice formulations containing the abrasives, dicalcium phosphate or calcium pyrophosphate, resulted in low plaque barrier activity and poor substantivity. It was speculated that the abrasive system could be the incompatible component. In fact, it has surprisingly been found that only nonabrasive gels wherein the principal gelling agent is a selected block copolymer of polyoxypropylene and polyoxyethylene are suitable oral hygiene delivery systems for the foregoing polysulfone resins in that only these gels, of all vehicle systems tested, have the combination of high plaque barrier activity, high substantivity and good aesthetic qualities. Desirable aesthetic properties for the gels of this invention can be defined as clarity, lack of cloudiness, a translucent gel possessing a firmness that prevents absorption or dissolution of the gel into toothbrush bristles. By contrast, poor aesthetics includes gel separation, precipitation of active ingredient and cloudiness of gel.

More particularly, this invention provides an oral hygiene composition for inhibiting the attachment of bacterial plaque to teeth, which comprises water, at least about 5% by weight of a humectant selected from the group consisting of glycerol and sorbitol, at least about 16% by weight of a gelling agent selected from the group consisting of the block copolymers of polyoxypropylene and polyoxyethylene wherein the polyoxypropylene component has a molecular weight in the range of from about 3,000 to about 4,000 and the polyoxyethylene comprises between about 25 and about 80 mole % of said copolymer, and from about 0.5 to about 10% by weight of a plaque barrier agent, which is a sulfonated poly(arylene ether sulfone) polymer having repeating units selected from the group consisting of structure (A),

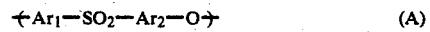

(A)

and structure (B),

(B)

wherein $Ar_1$ and $Ar_2$ are each selected from:

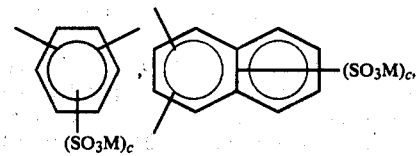

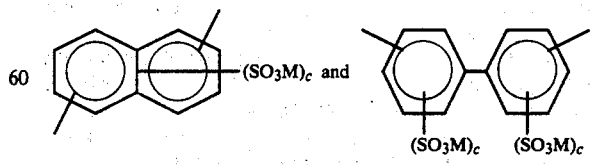

provided further that $Ar_2$ also can comprise one or more spacing units selected from —$Ar_4$—$SO_2$—$Ar_4$— and —$Ar_4$—$SO_2$—$Ar_4$—$SO_2$—$Ar_4$—, each $Ar_4$ in said spacing units being separately selected from:

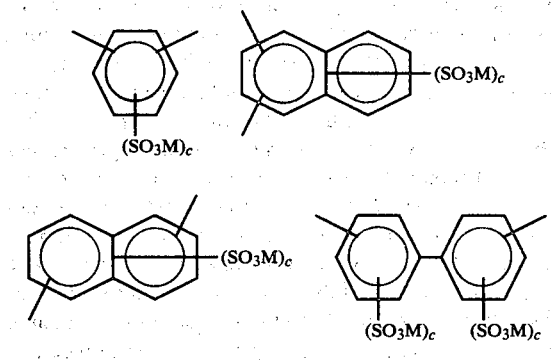

Ar₃ is selected from Ar₄ and

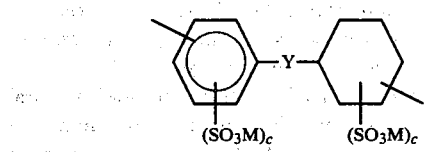

where Y is selected from lower alkylene having 1-5 carbon atoms, lower alkylidine having 2-5 carbon atoms,

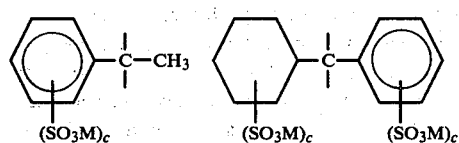

O, S, and SO₂; subscript c being an integer selected from 0, 1, and 2, the quotient, obtained by dividing the total number of sulfonate groups (i.e. the sum of the c's within each of repeating units (A) and (B) by the number of aromatic groups in said repeating unit, being (on the average) at least about 0.2; and M is selected from the group consisting of lithium, sodium, potassium, calcium, magnesium, zinc, aluminum, hydrogen, ammonium, and substituted ammonium ions derived from pharmaceutically acceptable organic amines.

The plaque barrier agents are present in these formulations in effective concentrations in the range of from about 0.5 to about 10 weight percent. A more preferred range is from about 2 to about 8 percent by weight, about 5% being the presently most preferred concentration.

Examples of specific, commercially available polyoxypropylene/polyoxyethylene block copolymer gelling agents within the foregoing definition are Pluronic F-127, Pluronic F-108, Pluronic P-103, Pluronic-104, Pluronic P-105, and Pluronic P-123. Effective gelling agent concentrations are generally between about 16% and 22% by weight.

The pH of these plaque barrier preparations should be between pH 5.0 and 10.0, preferably between pH 5.0 and 8.0, more preferably between about pH 6.0 and 7.5. Lower pH than 5.0 is undesirable because of the possible enhancement of enamel demineralization.

Suitable conventional pharmaceutically acceptable ingredients that may optionally be included in the barrier compositions of this invention are such humectants as polypropylene glycol, glycerol and sorbitol. When used, these humectants are generally present in the compositions in an amount of from about 5 to about 25% by weight. Other suitable additives include gel stabilizers such as the silicon dioxides, for example, Cab-O-Sil M5 and polyvinylpyrrolidone (generally 0.75–2.0 weight %); sweeteners such as sodium saccharin (usually about 0.1–0.3 weight %); preservatives such as citric acid, sodium benzoate, cetylpyridinium chloride, potassium sorbate, methyl and ethyl parabens (about 0.25–0.5 weight %); and approved colors (about 0.5–1% weight %) and flavors is a compatible fluoride salt for use as an anti-caries agent, for example, sodium fluoride.

In general, the metal and ammonium salts of the sulfonated poly(arylene ether sulfone) polymers are preferred as plaque barriers over the free sulfonic acid forms of the polymers because of their higher water solubility and lower degree of acidity, thereby favoring their use in oral hygiene formulations as dental plaque control barriers. The zinc salts are particularly preferred.

Hydrophilic, polymeric, anionic sulfonates useful for dental plaque control in accordance with the present invention are prepared by aromatic sulfonation of poly (arylene ether sulfone) polymers, followed by conversion of the polymeric sulfonic acid derivatives to metal salts of certain of the Group IA alkali metals, Group IIA, IIB, and IIIA multi-valent metals, and ammonium or amine-salts.

The polymers utilized for conversion to sulfonate derivatives are available either commercially or synthesized by known procedures found in the literature. Representative examples of commercial poly (arylene ether sulfone) polymers which can be sulfonated to the hydrophilic, anionic sulfonates used in the compositions of this invention are the following:

(a) Udel ® Polysulfone, type P1700 or medical grade MG11, available from Union Carbide Corp. in a molecular weight of about 35,000, and having the following repeating unit structure:

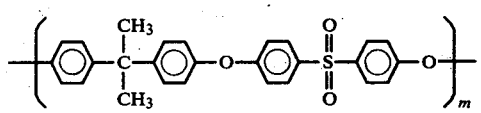

(b) Victrex ™ Polyethersulfone, grades 100P, 200P, 300P, from ICI America, Inc.:

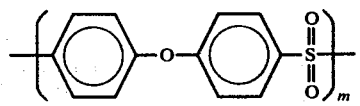

(c) Radel ® Polysulfone from Union Carbide Corp., and thought to have the following repeating unit structure:

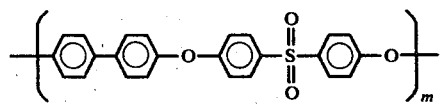

The generalized structures for other poly (arylene ether sulfone) polymers that can be sulfonated to form the sulfonated polymers used in the compositions of this invention are represented as formulas (I) and (II), and their method of synthesis is indicated in equations (1) and (2) below:

(I)  (II)

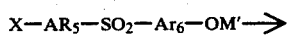 (1)

 + M'X

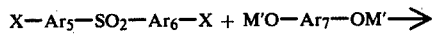 (2)

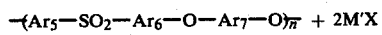 + 2M'X wherein X is a halogen; M' is a univalent metal such as sodium or potassium;

$Ar_5$ and $Ar_6$ are each selected from:

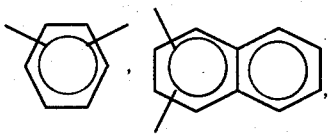

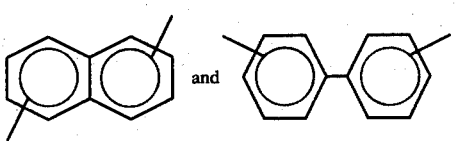

provided further that $Ar_6$ also can comprise one or more spacing units selected from $-Ar_8-SO_2-Ar_8-$ and $-Ar_8-SO_2-Ar_8-SO_2-Ar_8-$, each $Ar_8$ in said spacing units being separately selected from:

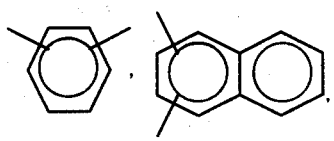

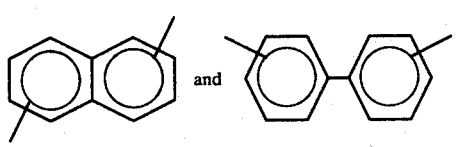

$Ar_7$ is selected from $Ar_8$ and:

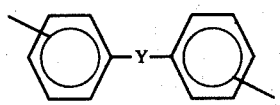

where Y is selected from lower alkylene having 1–5 carbon atoms, lower alkylidine having 2–5 carbon atoms,

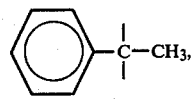

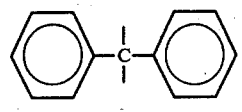

O, S, and $SO_2$.

Polymers of structure (I) can be synthesized by the general procedure (summarized in equation (1) above) described by T. E. Attwood, et al., in Polymer, Volume 18, pages 354–374 (1977). Polymers of structure (II) are prepared by reaction of bis(haloaryl) sulfones with univalent metal salts of aromatic diols, such as the reaction taught by R. N. Johnson, et. al., J. Polymer Science, Part A-1, Volume 5, pp 2375–2398 (1967). Poly (arylene ether sulfone) polymers suitable for conversion to sulfonated derivatives for use in the compositions and method of the present invention can be synthesized by varying the nature of the aromatic group, orientation of the linkages on the aromatic ring, and spacing of the sulfone ($SO_2$), ether (0) and other connecting groups in accordance with the foregoing definitions of the aromatic polymeric structures (I) and (II).

The sulfonation of poly (arylene ether sulfone) polymers, such as Udel ® Polysulfone, to water insoluble sulfonated polymers with low degrees of sulfonation, that are suitable as membranes for water desalination, have been described in the literature and patent publications such as A. Noshay and L. M. Robeson, J. Applied Polymer Science, 20, 1885–1903 (1976); C. L. Brousse, et. al., Desalination, 18, 137–153 (1976); and U.S. Pat. No. 3,709,841 (issued Jan. 9, 1973), U.S. Pat. No. 3,855,122 (issued Dec. 17, 1974), and U.S. Pat. No. 3,875,096 (issued Apr. 1, 1975). The sulfonated polysulfones reported in this literature differ from the polymeric materials employed in the compositions of the present invention in that they are substantially water insoluble, due to the relatively low degree of sulfonation, and therefore cannot be utilized in the aqueous media required for oral hygiene applications. As will be described hereinafter, the poly(arylene ether sulfone) sulfonates of the present invention are at least partially soluble in water or mixed solvents comprising water and an organic solvent miscible therewith (generally at least 1% w/w) and hydrophilic as a consequence of their higher degree of sulfonation. As discussed in greater detail hereinafter the degree of sulfonation (D.S.) also has a significant effect on the extent of dental plaque deposition. D.S. as used herein is the average number of sulfonate or sulfonic acid groups per repeating unit of the polymeric structure.

Preferred sulfonation agents for preparing the sulfonated polymeric barriers used in the compositions of this invention are anhydrous sulfur trioxide, triethyl phosphate (TEP) complexes of sulfur trioxide, and chlorosulfonic acid. Sulfonations can be effected in solvents such as methylene chloride, 1,2-dichloroethane, and chloroform. Temperature control of the sulfonation reaction with sulfur trioxide and its complexes with TEP is not very critical. Acceptable results are obtained over a $-20°$ C. to $+40°$ C. range. Sulfonations are generally effected at ambient room temperatures, since the sulfonation exotherm is very mild and rarely results in temperature increases beyond 35° C.

Typical impurities in the sulfonated polymer are small amounts of unreacted polymer, excess sulfonation agent (as sulfuric acid), and residual triethyl phosphate which are occluded in the solid polymer. Substantial purification is effected by slurrying the polymeric sulfonic acid derivatives in non-solvents therefor, such as the halocarbons. The preferred process for purification of the sulfonated polymers (both free acids and salts), particularly highly water soluble types, is by dialysis of their aqueous solutions in membrane tubes or hollow fiber dialyzing units having a molecular weight cut-off well below the molecular weight of the polymer. Dialysis removes all of the low molecular weight impurities, triethyl phosphate, and inorganic salts. High purity polymers are isolated as solids by freeze-drying or spray drying and dialyzed polymer solution.

Examples of pharmaceutically acceptable metal salts of the polymeric sulfonic acid derivatives of poly (arylene ether sulfone) polymers that can be used in oral hygiene compositions in accordance with this invention are the potassium, lithium, sodium, calcium, magnesium, zinc, and aluminum salts. The zinc salts are particularly preferred, since they exhibit higher substantivity to human dental enamel (after repeated washings with water) than the alkali metal salts. Other acceptable salt forms of the polymers are the ammonium salts prepared from ammonia or pharmaceutically-acceptable organic amines.

The alkali metal salts of the sulfonated polymers are conveniently prepared by neutralization of a water or alcohol solution of the polymeric sulfonic acid derivative with alkali metal hydroxide solutions to the potentiometric endpoint. The salts are recovered by filtration, solvent stripping, or freeze drying, depending on the type of solvent used and whether the salt precipitates directly from the solvent medium. Alternatively, sulfonate salts can be prepared by addition of at least stoichiometric quantities of an alkali metal oxide, carbonate, acetate, chloride, nitrate, or sulfate to the sulfonic acid derivative. The salts either precipitate directly, or are isolated by solvent stripping. Purification of the sulfonate salt by dialysis is the preferred procedure for the more highly water soluble salts.

Multivalent metal salts, such as the calcium, magnesium, zinc, and aluminum salts, of the sulfonated polymers can be prepared by methods similar to those described above. In an alternate procedure, multivalent metal salts can be prepared by an ion-exchange reaction between the multivalent ion and either the free sulfonic acid or an alkali metal sulfonate derivative of the polymer.

Ammonium salts of the sulfonic acid polymer can be prepared by direct addition of ammonia or a primary, secondary, or tertiary organic amine.

The polymeric sulfonic acids are highly effective in reducing the deposition of plaque during in vitro testing, but these sulfonic acid polymers are too highly acidic to permit use in the oral environment unless suitably buffered. Also, salts of the polymeric sulfonic acids are preferred because of their increased solubility in aqueous media and lower degree of acidity. These salts exhibit approximately equivalent reduction of plaque deposition to that exhibited by the corresponding free acids when tested in vitro.

The in vitro test procedure we have employed for testing plaque barrier activity begins with growth of plaque in small jars containing sterilized trypticase media that has been supplemented with sucrose. Typically, ten jars are individually inoculated with 0.5 ml of unpooled freshly collected human plaque from 10 subjects. In a control series, a presterilized glass slide or an extracted human tooth is inserted into each jar. In the test series, the tooth or glass slide is pretreated with a 1% solution of the test compound (dissolved in water or other vehicle), allowed to dry in order to deposit a thin film of the compound on the surface, and the glass slide or tooth placed in the growth media. The jars are incubated under anaerobic conditions for two days at 37° C. The tooth or glass slide is removed, air dried, and stained with 0.5% FD and C #3 red dye solution to reveal the accumulated plaque deposits. The tooth or glass slide is scored for plaque density on a 0 to 5 scale. Plaque barrier activity is reported as the % of average plaque reduction, as compared to appropriate controls for ten subjects.

A test method used to evaluate substantivity, which is relatively simple to perform and suited to a multi-component gel formulation in accordance with the present invention, involves variations on the foregoing plaque barrier activity test and is summarized below:

Test A

1. Coat both sides of a clean glass slide with the test formula. Use a toothbrush to achieve a thin coating.
2. Place the coated glass slide into a jar of pre-inoculated plaque media.
3. Anaerobically incubate for 48 to 72 hours at 37° C.
4. Stain the plaque deposit on the glass slide by immersing it in a 0.15% solution of FD and C Red #3 for one minute.
5. Evaluate the plaque deposit on the glass slides, comparing the amount of deposit on untreated control slides to the amount of deposit on the treated slides. The difference is reported as the "Percent Inhibition of Plaque Attachment to Glass Slides".

Test B

Follow the method of Test A and make this modification—after coating the slide with the test formula, rinse with cool running (1.6 l/min.) tap water for 5 seconds (2.5 seconds/side).

Test C

Modify the previous test methods by rinsing the glass slide for 10 seconds (5 seconds/side).

Test D

Modify the test method by rinsing the glass slide for 20 seconds (10 seconds/side).

Test E

Modify the method of Test A in the following manner:

1. Coat both sides of a clean glass slide with the test formula. Use a toothbrush to achieve a thin coating.
2. Rinse the glass slide with cool running tap water (brushing while rinsing) until all the test formula is washed off (visual observation).
3. Place the glass slide into a jar of pre-inoculated plaque media.
4. Continue as in Test A.

A preferred in vitro test procedure utilized to establish the degree of substantivity of the sulfonated poly-(arylene ether sulfones), but difficult to employ with multi-component gel formulations such as those of the present invention, is based on measurement of the zeta potential of powdered human dental enamel which has been contacted with an aqueous solution of the polymeric zinc sulfonate compound. This microelectrophoresis technique involves measurement of adsorption isotherms by determining the zeta potential of dental enamel in the presence of increasing concentrations of the polymeric zinc sulfonate, all solutions being made in 0.0200 M sodium chloride. When Udel® Polysulfone zinc sulfonate of D.S. 1.8 was so tested, the resultant adsorption isotherms indicated that the surface potential of the tooth enamel particles became increasingly negative with increasing concentration of the zinc salt. A plateau value of about −40 mV was reached and indicated that the surface of the enamel was saturated with the polymeric anion. In the absence of any of the polymeric zinc salt, the zeta potential of dental enamel was about −10 mV. These experimental techniques established that the polymeric anion is indeed adsorbed on the enamel surface. In desorption studies designed to measure the degree of substantivity of the polymeric sulfonate, powdered enamel was contacted for a short time with a 0.1% weight/volume solution of the polymeric sulfonate and then, after measurement of the initial charge on the enamel particle, was washed successively with large volumes of 0.0200 M sodium chloride and the zeta potential measured after each wash.

The degree of sulfonation of the poly (arylene ether sulfone) polymer has a significant effect on the reduction of plaque deposition, and it is found that a certain minimal D.S. is required for development of adequate plaque barrier activity. The D.S. can be varied at will by adjusting the conditions of the sulfonation reaction, such as the molar ratio of sulfonating agent to polymer. The nature of the aromatic polymer repeating unit governs the maximum D.S. which can be achieved. Linking groups, such as ether, sulfone, and various organic radicals (see e.g. the definition of Y set forth above) attached to the aromatic rings in the polymer chain structure can have either a deactivating or activating effect on aromatic sulfonation. Electronic and steric effects determine the position of sulfonation as well as ease of sulfonation. These mechanistic considerations have been reviewed in general organics texts, such as that by R. T. Morrison and R. N. Boyd, "Organic Chemistry," Third edition, Allyn and Bacon, Inc., Boston, 1973. In the poly (arylene ether sulfone) polymers, the ether linkages activate sulfonation in the available ortho-positions of the adjoining aromatic rings; in contrast, the sulfone group will deactivate the aromatic rings to which it is bonded with respect to aromatic sulfonation.

The degree of sulfonation (D.S.) of the poly(arylene ether sulfone) derivative can be determined by any of several methods: (a) NMR analysis, (b) elemental analysis for sulfur to carbon ratio, or (c) direct titration of the sulfonic acid with standard sodium hydroxide. The NMR method is perhaps the more exact procedure, since it is not prone to interference by other impurities, such as with the acidimetric or elemental analyses.

The acidimetric procedure for D.S. determination involves titration of an accurately weighed two gram sample (±0.1 mg) of the sulfonic acid polymer, dissolved in about ten volumes of water, alcohol, or other solvents, with standardized sodium hydroxide to the potentiometric endpoint. The acidity, A, of the samples is expressed in milliequivalents/gram (meq/g). Using the acidity value, A., and the formula weight, R, of the unsulfonated repeat unit in the polymer, the D.S. is calculated from the following equations:

$$A = \frac{(\text{ml. of titrant})(\text{Normality})}{\text{sample weight, in grams}}$$

$$D.S. = \frac{(R)(A)}{1000 - 80A}.$$

A related concept to D.S. which is sometimes more useful in correlating polymer structure with plaque barrier activity is the average number of sulfonate or sulfonic acid groups per aromatic group in the repeating unit. This is simply the D.S. (as determined by the aforementioned procedures) divided by the number of aromatic groups in the repeating unit, i.e., D.S./Ar. For example, Udel® Polysulfone zinc sulfonate of D.S. 2.0 can be expressed as exhibiting a D.S./Ar of 0.5, since there are four aromatic groups within each repeating unit.

Generally, sulfonated poly (arylene ether sulfone) polymers of high plaque barrier activity are obtained only when the average number of sulfonate groups per armatic group (D.S./AR) within the polymer is at least about 0.2. Aside from being insoluble in water, the nonsulfonated polymeric intermediates exhibit no plaque barrier activity. Effective plaque barrier activity (plaque reduction of at least above 40%) is seen only when the hydrophilic properties of the polymer are increased by introduction of either sulfonic acid or sulfonate salt functional groups.

Among the advantages of the nonabrasive gel formulations of the present invention are the high level of plaque barrier activity and substantivity that are maintained in a clear, uniform aesthetically pleasing preparation that is acceptable for use as an oral hygiene product. Moreover, since such anticaries fluoride compounds as sodium fluoride can be incorporated in these compositions, they can be employed as the primary dentrifice in an oral hygiene prophylaxis program.

EXAMPLE 1

The following formulation illustrates a presently preferred nonabrasive gel composition containing a barrier agent in accordance with the present invention.

| Ingredients | % w/w | |
|---|---|---|
| Distilled Water | q.s. | |
| Sodium Saccharin (sweetener) | 0.20 | |
| Sodium Benzoate (preservative) | 0.30 | |
| FD&C Blue #1 (0.1 % aq. soln.) | 0.27 | |
| D&C Yellow #10 (0.5% aq. soln.) | 0.50 | |
| Gelling agent | 18.00 | |
| Glyerol (Humectant) | 20.00 | |
| Cab-O-Sil M5 (Silicon Dioxide) | 1.00 | |
| Plaque Barrier Agent | 5.00 | (dry basis) |
| Sodium Fluoride | 0.22 | |
| Flavor | 0.80 | |
| | 100.00 | |

While the details of preparing the above formulations are well within he skill of the art, a suggested procedure for preparing the gel formulation of this example will be described for completeness.

In a first container the water, sodium saccharin, sodium benzoate the dyes are mixed. Then the container is put into an ice bath. When the temperature reaches 6° C., the gelling agent is added and the contents mixed slowly until the gelling agent is dissolved. Then the solution is heated to 70° C.

Into a second container is added the glycerol. Then the Cab-O-Sil M5 is sprinkled in with mixing. Then the plaque barrier agent is added and mixing continued to a smooth paste. The paste is then heated in a water bath with mixing to a temperature of 70° C.

The contents of the first container are added to the second container and blended together until the batch is homogenous while maintaining a 70° C. temperature. Then the flavoring is added, all mixing is stopped, and the formulation allowed to settle for approximately one hour. If necessary to remove air bubbles, overnight refrigeration may be employed.

These compositions are preferably employed from one to three times daily in a routine oral hygiene program to prevent the attachment of plaque to the teeth.

Variations can, of course, be made without departing from the spirit or scope of the invention.

We claim:

1. An oral hygiene composition for preventing the deposition of bacterial plaque on teeth, which comprises water, at least about 5% by weight of a humectant selected from the group consisting of glycerol and sorbitol, at least about 16% by weight of a gelling agent selected from the group consisting of the block copolymers of polyoxypropylene and polyoxyethylene wherein the polyoxypropylene component has a molecular weight in the range of from about 3,000 to about 4,000 and the polyoxyethylene comprises between about 25 and about 80 mole % of said copolymer, and from about 0.5 to about 10% by weight of a plaque barrier agent, which is a sulfonated poly(arylene ether sulfone) polymer having repeating units selected from the group consisting of structure (A), $$+Ar_1-SO_2-Ar_2-O+ \quad (A)$$

and structure (B), $$+Ar_1-SO_2-Ar_2-O-Ar_3-O+ \quad (B)$$

wherein $Ar_1$ and $Ar_2$ are each selected from

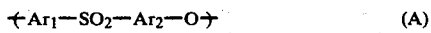

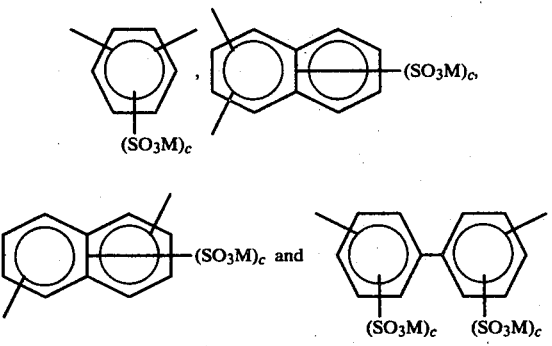

provided further that $Ar_2$ also can comprise one or more spacing units selected from $-Ar_4-SO_2-Ar_4-$ and $Ar_4-SO_2-Ar_4-SO_2-Ar_4-$, each $Ar_4$ in said spacing units being separately selected from:

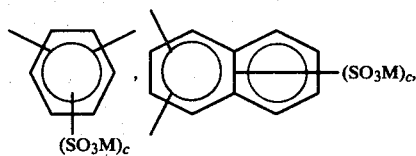

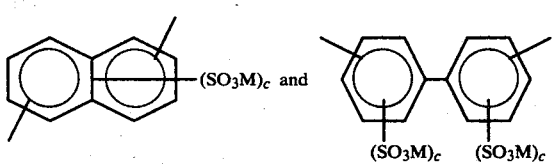

$Ar_3$ is selected from $Ar_4$ and:

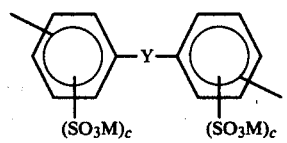

where Y is selected from lower alkylene having 1–5 carbon atoms, lower alkylidine having 2–5 carbon atoms,

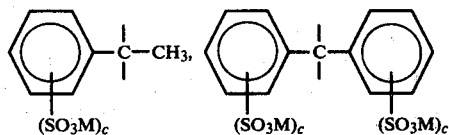

O, S, and $SO_2$; subscript c being an integer selected from 0, 1, and 2, the average quotient obtained by dividing the sum of the c's within each of repeating units (A) and (B) by the number of aromatic groups in said repeating unit being at least about 0.2; and M is selected from the group consisting of lithium, sodium, potassium, calcium, magnesium, zinc, aluminum, hydrogen, ammonium, and substituted ammonium ions derived from pharmaceutically acceptable organic amines.

2. The composition of claim 1 wherein M is a metal selected from the group consisting of potassium, lithium, sodium, calcium, magnesium, zinc and aluminum.

3. The composition of claim 1 wherein said plaque barrier agent is present in an amount of from about 2 to about 8 percent by weight.

4. The composition of claim 1 wherein the amount of said gelling agent is from about 16 percent to about 22 percent by weight.

5. A method of preventing deposition of dental plaque on teeth comprising periodically applying to the teeth a composition of claim 1.

6. The method of claim 5 wherein said composition is applied from about 1 to about 3 times per day.

* * * * *